United States Patent [19]

Haddad et al.

[11] Patent Number: 5,506,187
[45] Date of Patent: Apr. 9, 1996

[54] CATALYSTS FOR THE PRODUCTION OF MALEIC ANHYDRIDE BY THE OXIDATION OF BUTANE

[75] Inventors: Muin S. Haddad, Naperville, Ill.; Bernard L. Meyers, Wheaton; Hassan Taheri, Naperville; Philip A. Wolfe, Lisle, all of Ill.

[73] Assignee: Amoco Corporation, Chicago, Ill.

[21] Appl. No.: 247,328

[22] Filed: May 23, 1994

Related U.S. Application Data

[62] Division of Ser. No. 993,632, Dec. 18, 1992, abandoned.

[51] Int. Cl.$^6$ ..................................................... B01J 23/22
[52] U.S. Cl. .............................. 502/209; 502/353; 549/259
[58] Field of Search ................................. 502/209, 353; 549/239, 259

[56] References Cited

U.S. PATENT DOCUMENTS

| | | | |
|---|---|---|---|
| 4,515,904 | 5/1985 | Edwards | 502/209 |
| 4,517,371 | 5/1985 | Yang et al. | 549/239 |
| 4,732,885 | 3/1988 | Edwards et al. | 502/209 |

*Primary Examiner*—Anthony McFarlane
*Attorney, Agent, or Firm*—Mary Jo Kanady; Wallace L. Oliver

[57] ABSTRACT

A catalyst for the production of maleic anhydride by oxidation of butane and a process for the production of a catalyst using phosphoric acid and glycol ether solvents.

36 Claims, No Drawings

CATALYSTS FOR THE PRODUCTION OF MALEIC ANHYDRIDE BY THE OXIDATION OF BUTANE

This is a divisional of application Ser. No. 07/993,632, filed Dec. 18, 1992, now abandoned.

BACKGROUND OF THE INVENTION

The field of this invention relates to oxidation catalysts for the production of maleic anhydride as well as processes for the manufacture of phosphorus-vanadium, and phosphorus-vanadium-co-metal catalysts suitable for the oxidation of butane to maleic anhydride.

Maleic anhydride is of significant commercial interest throughout the world and is extensively used in the manufacture of alkyd resins. It is also a versatile intermediate for chemical synthesis. Consequently, large quantities of maleic anhydride are produced each year to satisfy these needs. The production of maleic anhydride by the catalytic oxidation of benzene and butene is well known, and until recently the principal method employed for the manufacture of maleic anhydride was by the air oxidation of benzene in the presence of certain heavy metal oxide catalysts. However, because of the inherent toxicity of benzene fumes, the trend has been to eliminate the utilization of benzene as a feedstock and newer facilities tend to utilize butane oxidation processes.

The present invention provides an oxidation catalyst for the manufacture of maleic anhydride. Further, the present invention provides a process for the manufacture of a phosphorus-vanadium, and phosphorus-vanadium-co-metal oxide catalysts by carrying out the reaction in a glycol ether solvent using phosphoric acid as a source of phosphorus.

The present invention provides a process for the manufacture of maleic anhydride in the presence of the catalyst manufactured by the novel process.

Vanadium phosphate butane oxidation catalysts are known and are described in U.S. Pat. Nos. 4,515,904, 4,652,543, and 4,732,885, all of which are incorporated herein by reference. The catalyst of the present invention provides several economic advantages over the prior vanadium phosphate butane oxidation catalysts. The prior catalysts use halogen-containing compounds, for example, chlorine-containing compounds. The inventive catalyst of the present invention does not use chlorine-containing compounds and, therefore, does not require expensive chlorine corrosion resistant manufacturing equipment. Further, chlorinated hydrocarbon byproducts are typically formed by the prior catalyst processes when the chlorine-containing compounds attack the solvent system used in the preparation of the catalyst. Since these chlorinated hydrocarbon byproducts are not formed by the present catalyst process, the solvent can be recycled and used to prepare additional catalyst. Thus, solvent supply costs and solvent disposal costs are greatly reduced.

In addition, while a calcination step may add improved properties to the catalyst of the present invention, the calcination step is not necessary for the practice of the present invention. Thus, one step of the prior catalyst preparation process can be eliminated to improve both efficiency and cost.

Briefly, our catalyst is suitably prepared in glycol ether solvents by:

(1) slurrying vanadium, phosphoric acid, and any additional metals or metal oxides with a glycol ether solvent;

(2) refluxing the slurry at from about 0° C. to about 200° C. for about 0.5 hours to about 6 hours, to reduce the vanadium from a plus five oxidation state to a plus four oxidation state which typically can be detected by a color change;

(3) drying the catalyst to substantially remove the solvent which can include standard drying techniques well known to those skilled in the art, for example oven or rotary drying;

(4) shaping the catalyst in the desired geometric shape; and (5) activating the catalyst.

The vanadium compound can be vanadium pentoxide, vanadium tetrachloride, vanadium trichloride, vanadium oxydichloride, vanadium oxytrichloride, vanadium tetraoxide, vanadium oxalate, and most soluble vanadium complexes. Additionally, suitable vanadium compounds include: vanadium oxides, such as vanadium trioxide and the like; vanadium oxyhalides, such as vanadyl chloride, vanadyl dichloride, vanadyl trichloride, vanadyl bromide, vanadyl dibromide, vanadyl tribromide and the like; vanadium-containing acids, such as meta-vanadic acid, pyrovanadic acid and the like; vanadium salts, such as ammonium meta-vanadate, vanadium sulfate, vanadium phosphate, vanadyl formate, vanadyl oxalate and the like; however, vanadium pentoxide is preferred.

In our catalyst preparation, various hydrous phosphoric acids (for example, 85% orthophosphoric acid) and anhydrous phosphoric acids (for example, 100% to 120% phosphoric acid) may be used. Suitable phosphoric acids including orthophosphoric acid, pyrophosphoric acid, triphosphoric acid, metaphosphoric acid, phosphorus pentoxide, and the like, or blends thereof. Orthophosphoric acid and polyphosphoric acids have been found to give a particularly useful catalyst. Polyphosphoric acids are phosphoric acids that are typically recognized to be a mixture of phosphoric acids, for example, a polyphosphoric acid that is commercially available from Albright and Wilson, Richmond Va., is approximately 54% $H_3PO_4$, 41% pyrophosphoric acid, and 5% triphosphoric acid.

The slurry can include additional metals or metal oxides such as molybdenum oxide, zinc oxide, uranium oxide, tungsten oxide, tin oxide, bismuth oxide, titanium oxide, chromium oxide, zirconium oxide, niobium oxide, antimony oxides and cobalt oxide in organic solvents, preferably organic ether solvents.

Suitable glycol ether solvents can be represented by Formula I $$R_1O\text{-}(R_2O)_n\text{H} \qquad \qquad \text{I}$$

wherein $R_1$ is a $C_1$ to $C_{12}$ alkyl or aryl moiety; $R_2$ is a $C_2$ to $C_{12}$ alkyl or aryl moiety; and n is from 1 to 5.

Preferably, $C_3$ to $C_8$ glycol ethers are used in the present invention. Most preferably, $C_3$ to $C_6$ glycol ethers are used in the present invention. Higher carbon number glycol ethers may result in logistical problems in the manufacture process. However, these problems may be avoided by further optimization of the reaction conditions. The solvents of Formula I are preferably liquids at ambient temperature.

Suitable solvents, according to Formula I, include ethylene glycol monomethyl ether, ethylene glycol monoethyl ether, ethylene glycol monopropyl ether, diethylene glycol monomethyl ether, propylene glycol monomethyl ether, and the like. We have found that ethylene glycol monomethyl ether (methoxyethanol), propylene glycol monomethyl ether (methoxypropanol), and diethylene glycol monomethyl ether are cost effective when used in the present invention.

Further, a cosolvent system can be prepared where two or more solvents of Formula I are present. For example, an ethylene glycol monomethyl ether and propylene glycol monomethyl ether cosolvent system can be used as shown in Example 8.

While the reaction solution is being refluxed, if desired a modifier or mixture of modifiers such as xylene, m-xylene, p-xylene, benzene, toluene, mesitylene, pseudocumene, phthalic anhydride, trimellitic anhydride, benzoic acid, toluic acid, phthalic acid isophthalic acid, terephthalic acid, trimesic acid, or trimellitic acid, is suitably added to the reaction solvent. After refluxing, the color of the syrup is typically light blue. The volume of the solution is dried, typically at a temperature of from about 120° C. to about 150° C. and from about 0 to about 30 inches of mercury vacuum under an optional air purge. Once dry, the color of the solid material is typically from blue-green to dark brown. The catalyst can be formed into geometric forms, such as cylinders, using graphite, Sterotex, or other lubricants such as steric acid, zinc stearate, or starch and binders such as polyvinyl alcohol.

The two important requirements of a good catalyst are low pressure drop and high yield. The size and shape of the tablets determine the void fraction available in a particular reactor. The void fraction should be large enough to avoid development of a large pressure drop across the reactor. One suitable catalyst form is a cylinder whose length and diameter are roughly equivalent and range in size from about 1/16 inch to about 1/2 inch In addition to its dependence on the shape and tablet dimensions, the reactors void fraction depends on whether these dimensions change at the high temperatures required for efficient conversion of butane. For example if the tablet undergoes a volume increase or "expansion," the void fraction will decrease and an unacceptable increase in pressure drop will result. Processes for reducing tablet expansion are known, for example, see U.S. Pat. Nos. 4,933,312, 4,957,894 and 5,019,545, all of which are fully incorporated herein by reference.

The catalyst in the form of geometric shapes or in powder form can be calcined in air or a nitrogen-air combination before loading into a suitable reactor, typically a tubular reactor. Calcining can be in dry or humid air, preferably in humid air. For example, see Example 16.

We have found that the introduction of water (from about 2 to about 100 wt. % of the total mass) into air during calcination results in faster catalyst activation and a higher maleic anhydride yield.

The catalyst is activated further by the addition of water and phosphorus compounds or mixtures thereof, such as alkylphosphates, phosphates, and phosphines, activating the catalyst by the addition of butane or another hydrocarbon feedstock and a phosphorus compound at a temperature of about 300° C. to about 500° C. Representative phosphorus compounds have the following structure:

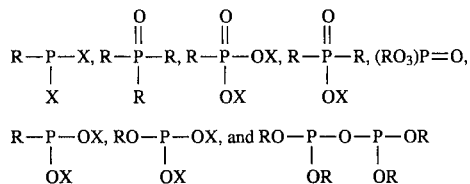

wherein R is a phenyl or an alkyl radical of 1 to 6 carbon atoms and X is H or R. Suitable compounds are primary, $RPH_2$, secondary, $R_2PH$, and tertiary, $R_3P$, phosphines, such as ethyl phosphine; the tertiary phosphine oxides, $R_3PO$, such as tripropyl phosphine oxide: the primary, $RP(O)(OX)_2$, and secondary, $RP(O)OX$, phosphonic acids, such as benzene phosphonic acid; the esters of the phosphonic acids, such as diethyl methanephosphonate; the phosphonous acids, $RPO_2X_2$, such as benzenephosphonous acid and the esters thereof, such as the monoethyl ester; the primary, $ROP(OX)_2$, secondary, $(RO)_2POX$, and tertiary, $(RO)_3P$, phosphites, such as diethyl phosphite, trimethyl phosphite, triethyl phosphite, triisopropyl phosphite, tripropyl phosphite, and tributyl phosphite, and the pyrophosphites, such as tetraethyl pyrophosphite. The preferred phosphous compound is an ester of orthophosphoric acid having the formula $(RO)_3P=O$ wherein R is hydrogen or a $C_1$ to $C_4$ alkyl, at least one R being a $C_1$ to $C_4$ alkyl. The preferred phosphorus compounds are triethylphosphate and trimethylphosphate.

The novel catalyst further comprises a phosphorus-vanadium mixed oxide or a phosphorus-vanadium mixed oxide promoted by metals. The atomic ratio of the vanadium to phosphorus can suitably be in the range of 0.5:1 to 1.25:1.0. The total atomic ratio of vanadium to phosphorus advantageously is in the range of 0.75:12 to 1:1. It is preferred that the total atomic ratio of molybdenum, zinc, tungsten, uranium, tin, bismuth, titanium, niobium, or cobalt to vanadium should be in the range of 0.001:1 to 0.2:1. The atomic ratio of phosphorus to vanadium is suitably in the range of 0.8:1 to 2:1, preferably 1:1 to 1.3:1.

The co-metal, such as molybdenum, zinc, tungsten, uranium, bismuth, titanium, zirconium, antimony, niobium, cobalt, chromium, or tin may be added as a compound together with vanadium, or separately introduced into the solution. Suitable co-metal compounds comprise their oxides and soluble salt. Suitable molybdenum compounds comprise molybdenum oxide and most soluble molybdenum salts. If it is desired to improve physical properties of the catalysts, they may be treated with the suspension of an inert support, for example, alumina, titania, silicon carbide, kieselguhr, pumice, or silica. The catalyst may be reinforced with such materials at any stage in its preparation.

The oxidation of butane to maleic anhydride may be accomplished by contacting n-butane in low concentration in oxygen with the described catalyst. Air is entirely satisfactory as a source of oxygen, but synthetic manufacturers of oxygen and diluent gases, such as nitrogen also may be employed. Air enriched with oxygen may be used.

The gaseous feed stream to the oxidation reactors will normally contain air and about 0.2 to about 1.7 mole percent of n-butane. About 0.8 to 1.5 mole percent of n-butane is satisfactory for optimum yield of maleic anhydride for the process of this invention. Although higher concentrations may be employed, explosive hazards may be encountered. Lower concentrations of butane, less than about one percent, of course, will reduce the total yield obtained at equivalent flow rates and, thus, are not normally economically employed. The flow rate of the gaseous stream through the reactor may be varied within rather wide limits, but preferred range of operations is at the rate of from about 100 cc to about 4000 cc of feed per cc of catalyst per hour, and more preferably from about 1000 cc to about 2400 cc of feed per cc of catalyst per hour. Residence times of the gas stream will normally be less than about four seconds, more preferably less than about one second, and down to a rate where less efficient operations are obtained. The flow rates and residence times are calculated at standard conditions of 760 mm of mercury at 25° C.

A variety of reactors will be found to be useful, and multiple tube heat exchanger-type reactors are quite satisfactory. These reactors may have a single or multiple cooling zones, for example a dual zone system. The diameter of such reactor may vary from about one-quarter inch to about three inches, and the length may be varied from about three to about sixteen or more feet. The oxidation reaction is an exothermic reactor and, therefore, relatively close control of the reaction temperatures should be maintained. It is desirable to have the surface of the reactors at relatively constant temperatures, and some medium to conduct heat from the reactors is necessary to aid temperature control. Such media may be Woods metal, molten sulphur, mercury, molten lead and the like, but it has been found that eutectic salt baths are completely satisfactory. One such salt bath is a sodium nitrate, sodium nitrite, potassium nitrate eutectic constant temperature mixture. An additional method of temperature control is to use a metal block reactor whereby the metal surrounding the tube acts as a temperature regulating body. As will be recognized by one skilled in the art, the heat exchanger medium may be kept at the proper temperature by heat exchangers and the like. The reactor or reaction tubes may be iron, stainless steel, carbon steel, nickel, glass tubes, such as vycor and the like. Both carbon steel and nickel tubes have excellent long life under the conditions of the reaction described herein. Normally, the reactors contain a preheat zone under an inert material such as one-quarter inch alundum pellets, inert ceramic balls, nickel balls, or chips and the like present at about one-half to one-tenth the volume of the active catalyst present.

The temperature of reaction may be varied within some limits, but normally the reaction should be conducted at a temperature within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than from about 20° F. to about 50° F. above the salt bath temperature. The temperature of the reactor, of course, will also depend to some extent upon the size of the reactor and the butane concentration.

The reaction may be conducted at atmospheric, superatmospheric, or below atmospheric pressure. The exit pressure will be at least slightly higher than the ambient pressure to ensure a positive flow from the reactor. The pressure of the inert gases must be sufficiently high to overcome the pressure drop through the reactor.

Maleic anhydride may be recovered by a number of ways well known to those skilled in the art. For example, the recovery may be by direct condensation or by absorption in suitable media, with specific operations and purification of the maleic anhydride.

The following examples will serve to provide full understanding of the invention, but it is to be understood that these examples are given for illustrative purposes only and will not be interpreted as limiting the invention in any way.

EXAMPLES

In the examples the terms "conversion", "selectivity" and "yield" are defined as follows:

$$\text{Conversion \%} = \frac{\text{Moles n-butane reacted}}{\text{Moles n-butane in feed}} \times 100$$

$$\text{Selectivity \%} = \frac{\text{Moles maleic anhydride produced}}{\text{Moles n-butane feed consumed}} \times 100$$

-continued
$$\text{Yield Wt. \%} = \frac{(\text{Conversion}) \times (\text{Selectivity})}{100} \times 1.69$$

To a 12-liter, 4-neck, round bottom flask equipped with a thermowell, electrical mantle, mechanical stirrer, and a reflux condenser, was added 728 g $V_2O_5$, 34.5 g $MoO_3$, 540 g $H_2O$, and 2000 ml tetrahydrofuran (THF). $POCl_3$ (1534 g) was added from an addition funnel over a period of two hours. During the $POCl_3$ addition, an exothermic reaction occurred which resulted in a continuous temperature rise, reflux of the solvent, and dissolution of the solids. The mixture turned from a yellow-orange slurry to a red-brown solution as the $POCl_3$ addition progressed. At the end of the $POCl_3$ addition, the deep green solution was heated up to reflux and maintained at reflux for two hours. The thick black syrup was then dried overnight at 180° C. in about a 3 inch vacuum with a mild air or a 92 mol % $N_2$/8 mol % $O_2$ purge passing during the oven.

The dark brown catalyst was then ground to less than 18 mesh and calcined in a fluid-bed calciner at 300° C. in air. In a typical calcination, dry air at 21 liters/minute was passed through a glass tube containing about 350 g of catalyst powder. The tube was heated up by surrounding furnace from ambient to 300° C. in about an hour. The speed of heat-up depended on the extent of the observed initial exotherm. The fluidized catalyst powder was kept at 300° C. for four hours. The calcined powder was then formed into 3/16 inch cylindrical tablets using 5 wt. % graphite as a lubricant.

EXAMPLE 1

Preparation With Methoxyethanol

To a 3-liter, 3-neck, round bottom flask equipped with a thermowell, electrical mantle, mechanical stirrer, and reflux condenser, was added 182 g $V_2O_5$, 8.64 g $MoO_3$, 245 g crystalline 100% o-phosphoric acid, and 500 ml methoxyethanol. The reaction mixture was brought to reflux at 241° F. (116° C.) and refluxed for two hours. During this period, the temperature dropped slowly to a lined-out value of about 224° F. (107° C.). The color of the reaction mixture started out at brown-orange, changed to green at reflux and to light blue-green and light blue at the end of the two hour reflux. The syrup became royal-blue upon cooling. The syrup was dried for 16 hours at 180° C. in a vacuum oven. The dry catalyst cake was then ground and tabletted into 3/16 inch tablets using 5 wt. % graphite as lubricant.

EXAMPLE 2

Preparation With Methoxyethanol

A catalyst was prepared according to Example 1, except that reflux time was one hour.

EXAMPLE 3

Preparation With Methoxypropanol

To a 3-liter, 3-neck, round bottom flask equipped with a thermowell, electrical mantle, mechanical stirrer, and reflux condenser, was added 182 g $V_2O_5$, 8.64 g $MoO_3$, 245 g crystalline 100% o-phosphoric acid, and 600 ml methoxypropanol. The reaction mixture was brought to reflux at 241° F. (116° C.) and refluxed for five hours. During this period, the temperature dropped slowly to a lined-out value of about 223° F. (106° C.). The color of the reaction mixture started out at brown-orange, changed to deep olive green, then to dark creamy blue-green, and to dark creamy blue at the end of reflux. The syrup was dried for 16 hours at 180° C. in a vacuum oven. The dry catalyst cake was then ground and tableted into 3/16 inch tablets using 5 wt. % graphite as lubricant.

Table I illustrates a comparison of Comparative Example A (a catalyst made using chlorides) and the catalyst of the present invention, Example I.

TABLE I

Comparison of Analytical Data for Conventional and New Maleic Anhydride Catalysts

| Example | Carbon, wt. % | Chloride, wt % | (Energy Release J/g) |
|---|---|---|---|
| Uncalcined A | 6.73 | 1.22 | +826 |
| Calcined A | 2.84 | 0.86 | +253 |
| 1 | 1.2 | 0 | −87 |

Energy release was measured by Differential Scanning Calorimetry by heating a sample in air up to 580° C. at a rate of 5.0° C./minute.

The data in Table I indicates that relative to either uncalcined or calcined Comparative Example A the process of the present invention produced a catalyst that has lower carbon content, no chlorides, and an endothermic rather than exothermic energy release when heated in air. The lower carbon content and energy release of the new catalyst tends to obviate the need for a calcination step and reduces the possibility of catalyst damage during start-up. Furthermore, the lack of chlorides in the catalyst of the present invention eliminates the corrosion threat to plant equipment that is present when chlorides are released during catalyst start-up.

GC and IR analysis of recovered solvent indicated that the effluent or used solvent was about 83 wt. % pure when compared to the beginning solvent. Thus, the solvent can be recycled for additional production (see Example 14).

The catalytic performance of some catalysts was determined in a mini-reactor test. A 6 cc charge of tablets was loaded into a 0.62 inch diameter mini-reactor and evaluated with a feed of 1.1 mol. % n-butane in synthetic air at a VHSV of 1200 hr$^{-1}$. About 10,000 ppm of water was continually added to the reactor feedstream by passing it through a water saturator. The feed and effluent streams were analyzed by gas chromatography. Conversion, selectivity and yield are reported in Table II.

TABLE II

Butane Conversion to Maleic Anhydride Performance

| Example | Time on Stream Days | Temp. °F./°C. | Conv. Mol % | Sel. Mol % | Yield Wt. % |
|---|---|---|---|---|---|
| A | 27 | 785/418 | 88.9 | 64.8 | 97.1 |
|   | 33 | 785/418 | 90.8 | 63.9 | 97.9 |
|   | 45 | 769/409 | 91.5 | 65.4 | 101 |
| 1 | 28 | 790/421 | 90.4 | 65.3 | 99.6 |
|   | 33 | 776/413 | 91.6 | 66.1 | 102 |
|   | 40 | 763/406 | 89.0 | 67.4 | 101 |
| 2 | 27 | 793/423 | 87.2 | 64.9 | 95.5 |
|   | 37 | 793/423 | 92.0 | 62.9 | 97.6 |
|   | 46 | 768/409 | 91.5 | 65.5 | 101 |
| 3 | 28 | 792/422 | 85.1 | 65.4 | 93.9 |
|   | 38 | 789/421 | 88.6 | 66.7 | 100 |
|   | 45 | 791/422 | 91.7 | 65.3 | 101 |

Table II illustrates the butane oxidation to maleic anhydride performance of catalysts made according to Comparative Example A and Examples 1–3. The data indicates that the maleic anhydride yield of catalysts made according to the new process in Examples 1–3 are comparable to the conventional catalyst (made using chlorides) depicted as Comparative Example A. This indicates that the advantages of the new process (without chlorides) are obtained without a detrimental effect on catalyst's performance.

EXAMPLE 4

Preparation With Methoxyethanol and 100% o-$H_3PO_4$

To a 3-liter, 3-neck, round bottom flask equipped with a thermowell, electrical mantle, mechanical stirrer, and reflux condenser was added 182 g $V_2O_5$, 8.64 g $MoO_3$, and 500 ml 2-methoxyethanol. The reaction mixture was brought to reflux, at which point slow addition of a solution of 245 g of 100% o-$H_3PO_4$ in 150 ml methoxyethanol was started. This solution was added in four increments in about one hour. Reflux was then continued for two additional hours. The thick creamy light blue syrup was dried for 16 hours 180° C. in an air purged vacuum oven under 15 inch of vacuum. The dry cake was then ground and tableted into 3/16 inch tablets containing 5 wt. % graphite as lubricant.

EXAMPLE 5

Preparation With Methoxypropanol and 100% o-$H_3PO_4$

To a 3-liter, 3-neck, round bottom flask equipped with a thermowell, electrical mantle, mechanical stirrer, and reflux condenser was added 182 g $V_2O_5$, 8.64 g $MoO_3$, 245 g 100% o-$H_3PO_4$, and 600 ml 1-methoxy-2-propanol. The reaction mixture was brought to reflux at 241° F. (116° C.). Reflux was continued for five hours. The thick creamy light blue syrup was dried for 16 hours at 180° C. in an air purged vacuum oven under 15 inch of vacuum. The dry cake was then ground and tableted into 3/16 inch tablets containing 5 wt. % graphite as lubricant.

EXAMPLE 6

Preparation With Methoxyethanol and 85% o-$H_3PO_4$

To a 3-liter, 3-neck, round bottom flask equipped with a thermowell, electrical mantle, mechanical stirrer, and reflux condenser was added 182 g $V_2O_5$, 8.64 g $MoO_3$, 144.1 g 85% $H_3PO_4$, and 700 ml methoxyethanol. The reaction mixture was brought to reflux at which point slow addition of 144.1 g 85% O-$H_3PO_4$ was started. This addition was completed in about 30 minutes. Reflux was then continued for 1.5 hours. The reflux temperature changed from 234° F. (112° C.) to 222° F. (106° C.) over the entire phosphoric acid addition and reaction reflux. The light creamy blue syrup was dried for 16 hours at 180° C. in an air purged vacuum oven under 15 inch of vacuum. The dry cake was then ground and tableted into 3/16 inch tablets containing 5 wt. % graphite as lubricant.

EXAMPLE 7

Preparation With Methoxyethanol and 85% o-$H_3PO_4$

This preparation of Example 7 was similar to Example 6 except that the reaction mixture contained 216.15 g 85% o-$H_3PO_4$, and 72.05 g 85% o-$H_3PO_4$ added slowly over about 30 minutes.

EXAMPLE 8

Preparation With Methoxyethanol/Methoxypropanol and 105% Polyphosphoric Acid Polyphosphoric acid is typically recognized to be a mixture of phosphoric acids, for example, a polyphosphoric acid that is commercially available from Albright and Wilson, Richmond Va., is approximately 54% $H_3PO_4$, 41% pyrophosphoric acid, and 5% triphosphoric acid.

To a 3-liter, 3-neck, round bottom flask equipped with a thermowell, electrical mantle, mechanical stirrer, and reflux condenser was added 231.57 g 105% polyphosphoric acid and 11.22 g $H_2O$. This mixture was heated at 200° F. (93° C.) for 1 hour. The remaining reactants were then added. The reactants included 182 g $V_2O_5$, 8.64 g $MoO_3$, 250 ml methoxyethanol, and 250 ml methoxypropanol. Reflux was then established at about 231° F. (111° C.) and continued for two hours. The reflux temperature was 223° F. (106° C.) at the end of reflux. Although the reaction mixture thickened considerably one-half hour into reflux, it thinned out considerably for the remainder of reflux time. The thin light creamy blue syrup was dried for 16 hours at 180° C. in an air purged vacuum oven under 15 inch of vacuum. The dry cake was then ground and tabletted into 3/16 inch tablets containing 5 wt. % graphite as lubricant.

EXAMPLE 9

Preparation With Methoxyethanol and 105% Polyphosphoric Acid

To a 3-liter, 3-neck, round bottom flask equipped with a thermowell, electrical mantle, mechanical stirrer, and reflux condenser was added 231.57 g 105% polyphosphoric acid and 11.22 g $H_2O$. This mixture was heated at 200° F. (93° C.) for 1 hour. The remaining reactants were then added. These reactants included 182 g $V_2O_5$, 8.64 g $MoO_3$ and 500 ml methoxyethanol. Reflux was then established at about 244° F. (118° C.) at the end of reflux. The thick creamy blue syrup was dried for 16 hours at 180° C. in an air purged vacuum oven under 15 inch of vacuum. The dry cake was then ground and tabletted into 3/16 inch tablets containing 5 wt. % graphite as lubricant.

EXAMPLE 10

Preparation With Methoxyethanol and 105% Polyphosphoric Acid

Example 10 was prepared in a manner similar to Example 9, except 550 ml of methoxyethanol was used.

EXAMPLE 11

Preparation With Methoxypropanol and 105% Polyphosphoric Acid

To a 3-liter, 3-neck, round bottom flask equipped with a thermowell, electrical mantle, mechanical stirrer, and reflux condenser was added 182 g $V_2O_5$, 8.64 g $MoO_3$, 231.57 g 105% polyphosphoric acid, 11.22 $H_2O$ and 600 ml methoxypropanol. The reaction mixture was brought to reflux at 243° F. (117° C.) and continued for 3 hours. Although the reaction mixture thickened considerably in the first two hours of reflux, it thinned out for the remainder of reflux time. The light creamy blue syrup was dried for 16 hours at 180° C. in an air purged vacuum oven under 15 inch of vacuum. The dry cake was then ground and tabletted into 3/16 inch tablets containing 5 wt. % graphite as lubricant.

The catalytic performance of the catalysts made in Examples 4–11 was determined and is reported in Table III.

TABLE III

| | Butane Conversion to Maleic Anhydride | | | |
|---|---|---|---|---|
| Example | Time on Stream Days | Temp. °F./°C. | Conv. Mol % | Sel. Mol % | Yield Wt. % |
| 4 | 51 | 756/402 | 89.2 | 66.1 | 99.5 |
| 5 | 63 | 763/406 | 90.4 | 64.7 | 98.7 |
| 6 | 56 | 753/400 | 88.4 | 66.4 | 99.0 |
| 7 | 52 | 751/399 | 90.3 | 66.5 | 101 |
| 8 | 52 | 736/391 | 88.4 | 68.4 | 102 |
| 9 | 61 | 746/397 | 89.6 | 65.8 | 99.5 |
| 10 | 53 | 751/399 | 90.0 | 66.3 | 101 |
| 11 | 53 | 745/396 | 90.0 | 65.6 | 100 |

As can be seen in Table III, all catalysts exhibited high conversion and yields at reasonable reaction temperatures.

EXAMPLE 12

Preparation with Methoxyethanol and 105% Polyphosphoric Acid

To a 12-liter, 4-neck, round bottom flask equipped with a thermowell, electrical mantle, mechanical stirrer, and two pairs of reflux condensers, was added 926.28 g 105% polyphosphoric acid and 44.88 g $H_2O$. This mixture was heated at 200° F. (93° C.) for 1 hour.

The remaining reactants were then added. These included 728 g $V_2O_5$, 34.56 g $MoO_3$, and 2200 ml 2-methoxyethanol. Reflux was established at 237° F. (114° C.) and continued for 1.5 hours. During reflux, the temperature dropped to about 228° F. (109° C.). The light creamy blue syrup was then dried in an air purged vacuum oven at 180° C. for 16 hours. The dry catalyst cake was ground and tabletted into 3/16 inch tablets.

EXAMPLE 13

Preparation With Methoxyethanol and 105% Polyphosphoric Acid

Example 13 was prepared in a manner similar to Example 12, except 7/32 inch tablets were prepared from the dry powder.

COMPARATIVE EXAMPLE B

Comparative Example B was prepared in a manner similar to Comparative Example A, except the calcined powder was tabletted into 7/32 inch tablets.

EXAMPLE 14

Preparation With Recycled Solvent from Examples 12 and 13

The solvent collected from drying the catalyst syrups of Examples 12 and 13 was used to carry out further catalyst preparations. Analysis of the collected solvent showed it to be about 83 wt. % of the total solvent pure methoxyethanol and from about 7 wt. % to about 8 wt. % water, with the balance being the formate ester of methoxyethanol.

The procedure for making catalysts with the recycled solvent was similar to that described for Example 12. The dry powder was tableted into 7/32 inch tablets.

EXAMPLE 15

Catalyst Evaluations of Example 12–14 in Large Pilot Reactors

Catalyst loads of the Comparative Examples A and B and the catalysts from Examples 12 to 14 of the present invention were evaluated in 1 inch OD 16 foot long pilot plant reactors. These catalysts were evaluated in either the 3/16 inch tablet size or the 7/32 inch tablet size. In all cases the catalyst was subjected to 1.5 mol. % butane in air feed at 2,000 volume hourly space velocity and inlet pressures of from about 15 to about 20 psig. Water was added to the feed at a concentration of 10,000 ppm. A 5 ppm aqueous solution of triethyl phosphate was also added to the feed.

Tables III–V reports performance data for Examples 12–14.

TABLE III 16 foot Pilot Reactor Performance of Comparative Example A and Example 12

| HOS | Temp. °F./°C. | Example A | Temp. °F./°C. | Example 12 |
|---|---|---|---|---|
| 500 | 767/408 | C: 77.1 | 749/398 | C: 84.2 |
|  |  | S: 64.8 |  | S: 62.5 |
|  |  | Y: 84.3 |  | Y: 88.8 |
| 750 | 755/402 | C: 82.1 | 746/397 | C: 85.3 |
|  |  | S: 63.2 |  | S: 63.4 |
|  |  | Y: 87.5 |  | Y: 91.3 |
| 1000 | 762/406 | C: 84.6 | 751/399 | C: 87.7 |
|  |  | S: 62.7 |  | S: 64.6 |
|  |  | Y: 89.5 |  | Y: 95.6 |
| 1200 | 772/411 | C: 86.0 | 756/402 | C: 84.9 |
|  |  | S: 61.8 |  | S: 65.2 |
|  |  | Y: 89.67 |  | Y: 93.3 |

HOS is hours on stream; Temp. is reactor temperature; C is conversion in mol %; S is selectivity in mol %; and Y is yield in wt % based on normal butane fed to the reactor.

TABLE IV 16-ft. Pilot Reactor Performance of Comparative Example B and Example 15

| HOS | Temp. °F./°C. | Example B | Temp. °F./°C. | Example 13 |
|---|---|---|---|---|
| 500 | 778/414 | C: 74.8 | 784/418 | C: 78.4 |
|  |  | S: 65.9 |  | S: 65.1 |
|  |  | Y: 83.3 |  | Y: 86.2 |
| 750 | 775/413 | C: 80.2 | 740/393 | C: 78.0 |
|  |  | S: 62.9 |  | S: 66.6 |
|  |  | Y: 85.3 |  | Y: 87.8 |
| 1000 | 772/411 | C: 80.2 | 740/393 | C: 78.0 |
|  |  | S: 63.4 |  | S: 64.8 |
|  |  | Y: 91.7 |  | Y: 93.9 |
| 1200 | 768/409 | C: 85.0 | 771/411 | C: 86.6 |
|  |  | S: 62.1 |  | S: 64.4 |
|  |  | Y: 89.3 |  | Y: 94.3 |

HOS is hours on stream; Temp. is reactor temperature; C is conversion in mol %; S is selectivity in mol %; and Y is yield in wt % based on normal butane fed to the reactor.

TABLE V 16-ft Pilot Reactor Performance of Example 14 Catalyst Made in Recycled Solvent

| HOS | Temp. °F./°C. | C. Mol % | S. Mol % | Y. Wt. % |
|---|---|---|---|---|
| 505 | 772/411 | 75.10 | 67.0 | 85.1 |
| 777 | 772/411 | 79.4 | 65.8 | 88.4 |
| 941 | 775/413 | 84.8 | 64.2 | 92.0 |
| 1192 | 778/414 | 86.2 | 63.5 | 92.5 |

HOS is hours on stream; Temp. is reactor temperature; C is conversion; S is selectivity; and Y is yield. in wt. % based on normal butane fed to the reactor.

As can be seen from Tables III–V, the data shows that the performance of the catalysts made according to the present invention from fresh or recycled solvent is equivalent or better than that of the catalysts made according to Comparative Examples A and B.

EXAMPLE 16

Effect of Calcination in Humid Air

In a calcination study, the dry powders from Comparative Example A and Example 12 were calcined in a rotary calciner. The 4 inch ID 7.5 foot long calciner was rotated at 3 rpm at an inclination of 2 degrees. For Comparative Example A, the skin temperature was set at about 800° F. (427° C.) and for Example 12 powder, the skin temperature was set at 550° F. (288° C.). In both cases, the powder was calcined in three passes at a feed rate of about 1 lb/hr. Three calcinations were performed. In the first, the Comparative Example A powder was calcined in dry air at an air rate of 150 liters/hr. In the second calcination, Comparative Example A powder was calcined while water was added to the air at 260 gr/hr. In the third calcination, the powder of Example 12 was calcined at an air rate of 150 liters/hr and water rate of 260 g/hr.

Mini-reactor performance data of Comparative Example A powder calcined in dry and humid air and for Example 12 before and after calcination in humid air are shown in Tables VI and VII, respectively.

TABLE VI

Mini-Reactor Performance Data For Comparative Example A Powder Calcined in Dry and Humid Air

| Days on Steam | Temp.°F./°C. | C. Mol % | S. Mol % | Y. Wt. % |
|---|---|---|---|---|
| Calcined in Dry Air |  |  |  |  |
| 9 | 767/408 | 78.3 | 65.6 | 86.6 |
| 24 | 786/419 | 82.2 | 66.4 | 92.1 |
| 45 | 788/420 | 85.6 | 66.0 | 95.4 |
| 72 | 776/413 | 90.4 | 64.1 | 97.8 |
| Calcined in Humid Air |  |  |  |  |
| 9 | 773/412 | 86.72 | 64.9 | 94.9 |
| 25 | 783/417 | 88.3 | 65.2 | 97.0 |
| 46 | 770/410 | 90.6 | 65.8 | 100.5 |
| 70 | 745/396 | 89.6 | 66.4 | 100.4 |

Temp. is temperature; C is conversion; S is selectivity and Y is yield.

TABLE VII

Mini-Reactor Performance Data For Example 12
Before and After Calcination in Humid Air

| Days on Steam | Temp.°F./°C. | C. Mol % | S. Mol % | Y. Wt. % |
|---|---|---|---|---|
| Before Calcination | | | | |
| 8 | 772/411 | 75.0 | 66.9 | 84.7 |
| 23 | 782/416 | 77.3 | 67.0 | 87.3 |
| 42 | 783/417 | 86.3 | 64.5 | 94.0 |
| 56 | 771/411 | 88.7 | 64.0 | 96.0 |
| After Humid Air Calcination | | | | |
| 8 | 770/410 | 81.7 | 65.7 | 90.6 |
| 24 | 781/416 | 83.4 | 67.0 | 94.0 |
| 42 | 773/412 | 89.8 | 65.4 | 99.0 |
| 56 | 758/403 | 89.6 | 66.9 | 101 |

Temp. is temperature; C is conversion; S is selectivity and Y is yield.

Tables VI and VII show that calcination of both catalysts in humid air results in attaining a higher yield at an earlier time. Furthermore, the activity of the catalyst is increased as a result of humid air calcination as reflected by the lower temperature required to attain about the same conversion.

This invention has been described in terms of specific embodiments set forth in detail. It should be understood, however, that these embodiments are presented by way of illustration only, and that the invention is not necessarily limited thereto. Modifications and variations within the spirit and scope of the claims that follow will be readily apparent from this disclosure, as those skilled in the art will appreciate.

That which is claimed is:

1. A chloride-free catalyst made by the process consisting essentially of reacting at a temperature of about 0° C. to about 200° C. a vanadium compound in a glycol ether solvent with a phosphoric acid, eliminating the glycol ether solvent, and activating the catalyst by the addition of butane or another hydrocarbon feedstock and a phosphorus compound at a temperature of about 300° C. to about 500° C. wherein the weight ratio of any added water to catalyst present prior to activating the catalyst is less than 1.

2. A chloride-free phosphorous-vanadium oxide catalyst suitable for use in the manufacture of maleic anhydride from butane which is prepared by the process consisting essentially of reacting at a temperature of about 0° C. to about 200° C. a vanadium compound in a glycol ether solvent with a phosphoric acid, substantially removing the glycol ether solvent, and activating the catalyst by the addition of butane or another hydrocarbon feedstock and a phosphorus compound at a temperature of about 300° C. to about 500° C. wherein the weight ratio of any added water to catalyst present prior to activating the catalyst is less than 1.

3. A catalyst according to claim 2 wherein the vanadium compound is vanadium pentoxide.

4. A catalyst according to claim 2 wherein the catalyst is calcined in humid air prior to activating the catalyst.

5. A catalyst according to claim 2 wherein the phosphoric acid is selected from the group consisting of hydrous phosphoric acids and anhydrous phosphoric acids.

6. A catalyst according to claim 5 wherein the phosphoric acid is selected from the group consisting of orthophosphoric acid and polyphosphoric acid.

7. A catalyst according to claim 2 wherein the glycol ether solvent is selected from the group consisting of ethylene glycol monomethyl ether, propylene glycol monomethyl ether, and diethylene glycol monomethyl ether.

8. A catalyst according to claim 2 wherein the glycol ether solvent is a solvent system having two or more solvents of formula $$R_1O\text{-}(R_2O)_n\text{-}H \qquad \text{I}$$

wherein $R_1$ is a $C_1$ to $C_{12}$ alkyl or aryl moiety; $R_2$ is a $C_2$ to $C_{12}$ alkyl or aryl moiety; and n is from 1 to 5.

9. A catalyst according to claim 2 wherein the catalyst is suspended on an inert support.

10. A catalyst according to claim 9 wherein the inert support is selected from the group consisting of alumina, titania, silicon carbide, kieselguhr, pumice, and silica.

11. A chloride-free phosphorous-vanadium oxide catalyst suitable for use in the manufacture of maleic anhydride from butane which is prepared by the process consisting essentially of:

(1) slurrying a pentavalent vanadium compound and phosphoric acid with a glycol ether solvent;

(2) refluxing the slurry at from about 0° C. to about 200° C. for about 0.5 hours to about 6 hours to reduce the vanadium from a plus five oxidation state to a plus four oxidation state;

(3) drying the catalyst to substantially remove the solvent;

(4) shaping the catalyst in the desired geometric shape; and (5) activating the catalyst by the addition of butane or another hydrocarbon feedstock and a phosphorus compound at a temperature of about 300° C. to about 500° C.;

wherein the weight ratio of any added water to catalyst present prior to activating the catalyst is less than 1.

12. A catalyst according to claim 11 wherein the shaping step produces a geometric shape comprising a cylinder whose length and diameter are approximately equivalent and range in size from about 1/16 inch to about 1/2 inch.

13. A catalyst according to claim 12 wherein the length and diameter of the cylinder are approximately 3/16 inch.

14. A catalyst according to claim 12 wherein the length and diameter of the cylinder are approximately 7/32 inch.

15. A catalyst according to claim 11 further including the addition of a co-metal in step (1).

16. A catalyst according to claim 2 further including the addition of a co-metal to the reaction mixture.

17. A catalyst according to claim 15 wherein the co-metal is selected from the group consisting of molybdenum, zinc, tungsten, uranium, bismuth, titanium, zirconium, antimony, niobium, cobalt, chromium, and tin.

18. A catalyst according to claim 17 wherein the co-metal is molybdenum.

19. A catalyst according to claim 16 wherein the co-metal is selected from the group consisting of molybdenum, zinc, tungsten, uranium, bismuth, titanium, zirconium, antimony, niobium, cobalt, chromium, and tin.

20. A catalyst according to claim 19 wherein the co-metal is molybdenum.

21. A chloride-free phosphorous-vanadium oxide catalyst suitable for use in the manufacture of maleic anhydride from butane which is prepared by the process consisting essentially of reacting at a temperature of about 0° C. to about 200° C. a vanadium compound in a glycol ether solvent with a phosphoric acid; substantially removing the glycol ether solvent; and activating the catalyst by the addition of butane or another hydrocarbon feedstock and a phosphorus compound at a temperature of about 300° C. to about 500° C.;

wherein the preparation of the catalyst is conducted in the substantial absence of added water prior to activating the catalyst.

22. A catalyst according to claim 1 wherein the catalyst is made in the substantial absence of added water prior to activating the catalyst.

23. A catalyst according to claim 11 wherein the preparation of the catalyst is conducted in the substantial absence of added water prior to activating the catalyst.

24. A chloride-free catalyst made by the process consisting essentially of reacting at a temperature of about 0° C. to about 200° C. a vanadium compound in a glycol ether solvent with a phosphoric acid, eliminating the glycol ether solvent, and activating the catalyst by the addition of butane or another hydrocarbon feedstock and a phosphorus compound at a temperature of about 300° C. to about 500° C.

25. A chloride-free phosphorous-vanadium oxide catalyst suitable for use in the manufacture of maleic anhydride from butane which is prepared by the process consisting essentially of reacting at a temperature of about 0° C. to about 200° C. a vanadium compound in a glycol ether solvent with a phosphoric acid, substantially removing the glycol ether solvent, and activating the catalyst by the addition of butane or another hydrocarbon feedstock and a phosphorus compound at a temperature of about 300° C. to about 500° C.

26. A chloride-free phosphorous-vanadium oxide catalyst suitable for use in the manufacture of maleic anhydride from butane which is prepared by the process consisting essentially of:

(1) slurrying a pentavalent vanadium compound and phosphoric acid with a glycol ether solvent;

(2) refluxing the slurry at from about 0° C. to about 200° C. for about 0.5 hours to about 6 hours to reduce the vanadium from a plus five oxidation state to a plus four oxidation state;

(3) drying the catalyst to substantially remove the solvent;

(4) shaping the catalyst in the desired geometric shape; and (5) activating the catalyst by the addition of butane or another hydrocarbon feedstock and a phosphorus compound at a temperature of about 300° C. to about 500° C.

27. A catalyst according to claim 25 wherein the vanadium compound is vanadium pentoxide.

28. A catalyst according to claim 25 wherein the catalyst is calcined in humid air prior to activating the catalyst.

29. A catalyst according to claim 29 wherein the glycol ether solvent is selected from the group consisting of ethylene glycol monomethyl ether, propylene glycol monomethyl ether, and diethylene glycol monomethyl ether.

30. A catalyst according to claim 29 further including the addition of a co-metal to the reaction mixture.

31. A catalyst according to claim 30 wherein the co-metal is selected from the group consisting of molybdenum, zinc, tungsten, uranium, bismuth, titanium, zirconium, antimony, niobium, cobalt, chromium, and tin.

32. A catalyst according to claim 26 wherein the vanadium compound is vanadium pentoxide.

33. A catalyst according to claim 26 wherein the catalyst is calcined in humid air prior to activating the catalyst.

34. A catalyst according to claim 26 wherein the glycol ether solvent is selected from the group consisting of ethylene glycol monomethyl ether, propylene glycol monomethyl ether, and diethylene glycol monomethyl ether.

35. A catalyst according to claim 26 further including the addition of a co-metal to the reaction mixture.

36. A catalyst according to claim 35 wherein the co-metal is selected from the group consisting of molybdenum, zinc, tungsten, uranium, bismuth, titanium, zirconium, antimony, niobium, cobalt, chromium, and tin.

\* \* \* \* \*

UNITED STATES PATENT AND TRADEMARK OFFICE
CERTIFICATE OF CORRECTION

PATENT NO.: 5,506,187

DATED: April 9, 1996

INVENTOR(S): Muin S. Haddad, Bernard L. Meyers, Hassan Taheri, Philip A. Wolfe It is certified that error appears in the above-identified patent and that said Letters Patent is hereby corrected as shown below:

| Col. | Line | |
|------|------|---|
| 3 | 30 | "reactors void fraction" should read --reactor's void fraction-- |
| 6 | 4 | --COMPARATIVE EXAMPLE A-- should be inserted above the paragraph that begins "To a 12-liter, 4-neck, round bottom flask" |

Signed and Sealed this

Twenty-third Day of July, 1996

Attest:

BRUCE LEHMAN

Attesting Officer

Commissioner of Patents and Trademarks